US009173781B2

(12) United States Patent
Otsubo et al.

(10) Patent No.: US 9,173,781 B2
(45) Date of Patent: Nov. 3, 2015

(54) DISPOSABLE WEARING ARTICLE

(75) Inventors: Toshifumi Otsubo, Kanonji (JP);
Tatsuya Hashimoto, Kanonji (JP);
Mariko Yamashita, Kanonji (JP);
Etsuko Kudo, Kanonji (JP); Akiko Tange, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 499 days.

(21) Appl. No.: 13/515,844

(22) PCT Filed: Jan. 6, 2011

(86) PCT No.: PCT/JP2011/050120
§ 371 (c)(1),
(2), (4) Date: Jun. 14, 2012

(87) PCT Pub. No.: WO2011/083822
PCT Pub. Date: Jul. 14, 2011

(65) Prior Publication Data
US 2012/0259307 A1 Oct. 11, 2012

(30) Foreign Application Priority Data

Jan. 8, 2010 (JP) .................................. 2010-003415
Jun. 11, 2010 (JP) .................................. 2010-134546

(51) Int. Cl.
*A61F 13/15* (2006.01)
*A61F 13/49* (2006.01)
*A61F 13/496* (2006.01)

(52) U.S. Cl.
CPC ......... *A61F 13/49017* (2013.01); *A61F 13/496* (2013.01); *A61F 13/49011* (2013.01); *A61F 13/49012* (2013.01); *A61F 13/4963* (2013.01); *A61F 2013/49022* (2013.01)

(58) Field of Classification Search
CPC .................. A61F 13/49049; A61F 13/49058; A61F 13/4906; A61F 13/49061; A61F 2013/4518; A61F 2013/4525; A61F 2013/49074; A61F 2013/49076; A61F 13/49011; A61F 13/49012; A61F 13/49022; A61F 13/49033; A61F 13/49038; A61F 13/4963

USPC ............. 604/385.21, 385.22, 385.23, 385.24, 604/385.25, 385.26, 385.27, 385.29
See application file for complete search history.

(56) References Cited

U.S. PATENT DOCUMENTS 4,743,241 A     5/1988  Igaue et al.
6,146,367 A *  11/2000  Otsubo et al. ............ 604/385.01
(Continued)

FOREIGN PATENT DOCUMENTS

EP    2413865 A1    2/2012
EP    2526913 A1   11/2012
(Continued)

OTHER PUBLICATIONS

International Search Report for PCT/JP2011/050120 mailed Mar. 22, 2011.
Extended European Search Report issued Jun. 16, 2014, corresponds to European patent application No. 11731820.4.

*Primary Examiner* — Lynne Anderson
*Assistant Examiner* — Bradley Philips
(74) *Attorney, Agent, or Firm* — Hauptman Ham, LLP

(57) ABSTRACT

A disposable wearing article includes a front side edges lying in a front waist region, rear side edges lying in a rear waist region and crotch side edges lying in a crotch region. A chassis of the diaper includes a first backsheet forming the front waist region and a part of the crotch region and a second backsheet forming the rear waist region and a part of the crotch region. The front and rear waist regions are provided with first front and rear waist elastic yarns or threads and front and rear region elastic sheets, and the crotch region is provided along the crotch side edges with front and rear leg elastic elements. Ends of front leg elastic elements on one side overlap the front side edges. Ends of the rear leg elastic elements on one side overlap the rear side edges.

8 Claims, 9 Drawing Sheets

(56) References Cited

U.S. PATENT DOCUMENTS

| | | | |
|---|---|---|---|
| 6,464,677 B1* | 10/2002 | Noguchi et al. | 604/385.27 |
| 6,503,236 B1 | 1/2003 | Uitenbroek et al. | |
| 6,652,504 B1* | 11/2003 | Olson et al. | 604/385.25 |
| 7,632,259 B2* | 12/2009 | Elfstrom et al. | 604/385.27 |
| 8,377,024 B2* | 2/2013 | Desai et al. | 604/385.22 |
| 8,758,318 B2* | 6/2014 | Otsubo et al. | 604/385.25 |
| 2002/0152540 A1* | 10/2002 | Van Gompel et al. | 2/406 |
| 2005/0004549 A1 | 1/2005 | Maas et al. | |
| 2005/0136224 A1* | 6/2005 | Nickel et al. | 428/172 |
| 2005/0137563 A1* | 6/2005 | Van Gompel et al. | 604/385.27 |
| 2006/0064069 A1* | 3/2006 | Rajala et al. | 604/385.24 |
| 2008/0161765 A1* | 7/2008 | Morman et al. | 604/370 |
| 2008/0287899 A1* | 11/2008 | Morrell-Schwartz et al. | 604/365 |
| 2009/0062759 A1* | 3/2009 | Shimada et al. | 604/365 |

FOREIGN PATENT DOCUMENTS

| | | |
|---|---|---|
| JP | 63014506 | 1/1988 |
| JP | 08164164 | 6/1996 |
| JP | 2000166969 | 6/2000 |
| JP | 2002272785 | 9/2002 |
| JP | 2003306858 | 10/2003 |
| JP | 2003534041 | 11/2003 |
| JP | 2006230920 | 9/2006 |
| JP | 2006346439 | 12/2006 |
| JP | 2009207628 | 9/2009 |
| JP | 2010233733 A | 10/2010 |
| JP | 2011147608 A | 8/2011 |
| WO | 9611656 | 4/1996 |
| WO | 2009110153 | 9/2009 |
| WO | 2010113472 A1 | 10/2010 |

* cited by examiner

DISPOSABLE WEARING ARTICLE

RELATED APPLICATIONS

The present application is a national phase of PCT/JP2011/050120, filed Jan. 6, 2011 and is based on, and claims priority from, Japanese Application Numbers 2010-003415, filed Jan. 8, 2010 and 2010-134546, filed Jun. 11, 2010.

TECHNICAL FIELD

The present invention relates to disposable wearing articles and more particularly to disposable wearing articles using an elasticized sheet for a waist region such as disposable toilet-training pants, disposable incontinent pants, disposable sanitary pants and the like.

BACKGROUND

Conventionally, disposable diapers using elasticized sheets for front and rear waist regions to elasticize the front and rear waist regions in a transverse direction are known. For example, JP 2006-346439 A (PTL 1) discloses a disposable diaper having a chassis including a topsheet formed of a non-stretchable sheet and a backsheet formed of stretchable backsheet.

CITATION LIST

Patent Literature

{PTL 1} JP 2006-346439 A

SUMMARY

Technical Problem

According to the disclosure of PTL 1, the front and rear waist regions are joined together along respective opposite side edges so as to form a waist-opening and a pair of leg-openings, and the opposite side edges of the front and rear waist regions joined in this manner extend in a longitudinal direction substantially in parallel to each other. In such a diaper, when it is desired to put the diaper on the wearer's body, it is difficult to visually recognize the leg-openings from above the opened waist-opening and there is a possibility that the wearer's leg or legs might be caught by the lower end (s) of the side edge(s).

An object of the present invention is to provide a disposable wearing article having portions in front and rear waist regions adjacent to a crotch region broadened out in a transverse direction.

Solution to Problem

According to the present invention, there is provided a disposable wearing article having a longitudinal direction and a transverse direction and including:

a chassis including a side facing the wearer's body, a side facing away from the wearer's body, a first waist region which is one of front and rear waist regions, a second waist region which is the other of the front and rear waist regions and a crotch region extending between the first and second waist regions;

waist elastic elements serving to contractibly elasticize the first and second waist regions in the transverse direction; and leg elastic elements serving to contractibly elasticize the crotch region in the longitudinal direction wherein the first and second waist regions are joined together along respective opposite side edges thereof to form lines of side seams having stiffness higher than the remaining region and to form a waist-opening and a pair of leg-openings.

The improvement according to the present invention is characterized in that the leg elastic elements are formed of elasticized sheets each having opposite ends at least one of which overlaps associated one of the opposite side edges and having stiffness higher than the remaining region; and sections of the first and second waist regions adjacent to the crotch region and overlapping the leg elastic elements are broadened outward in the transverse direction.

According to one embodiment of the present invention, the waist elastic elements include first waist elastic yarns or threads formed of elastomeric elastic yarns or threads attached along the waist-opening and waist elastic sheets arranged closer than the first waist elastic yarns or threads to the crotch region and formed of elasticized sheets.

According to another embodiment of the present invention, the leg elastic elements arranged at least in one of the first and second waist regions do not overlap the waist elastic sheets and the waist elastic sheets are arranged between the first waist elastic yarns or threads and the leg elastic elements.

According to still another embodiment of the present invention, the leg elastic elements include first leg elastic elements extending from the first waist region to the crotch region and second leg elastic elements extending from the second waist region to the crotch region.

According to yet another embodiment of the present invention, the leg elastic elements are formed of a stretchable fibrous nonwoven fabric containing elastomeric fibers.

According to further another embodiment of the present invention, the chassis and the leg elastic elements are joined together by the lines of side seams.

According to one alternative embodiment of the present invention, the waist elastic elements include second waist elastic yarns or threads formed of elastic yarns or threads made of elastomer material overlapping the leg elastic elements and extending in the transverse direction.

According to another alternative embodiment of the present invention, the chassis includes backsheets lying on the side facing away from the wearer's body and the backsheets contains crimped fibers and are formed with a plurality of thermal compression bonded regions.

Advantageous Effects of Invention

According to the present invention, particularly to one or more embodiments thereof, the leg elastic elements formed of the elasticized sheets are arranged so that the ends thereof on the sides extending into the respective waist regions overlap the side edges of the chassis. With this unique arrangement, these overlapping portions have stiffness higher than the remaining region. When the front and rear waist regions contract in the transverse direction under contraction of the waist elastic elements, the portion on the side of the waist-opening and defined above the overlapping ends are noticeably contracted under contraction of the waist elastic elements and the portion on the side of the leg-openings and defined by the overlapping ends are not noticeably contracted. In consequence, the elasticized sheets are broadened outward in the transverse direction and toward the leg-openings. In this way, when putting the diaper on the wearer's body, the leg-openings can be visually recognized from above through the waist-opening and it is possible to prevent the wearer's leg or legs from being caught by the lower ends of the diaper's side edges.

DESCRIPTION OF EMBODIMENTS

First Embodiment

Figure 1:
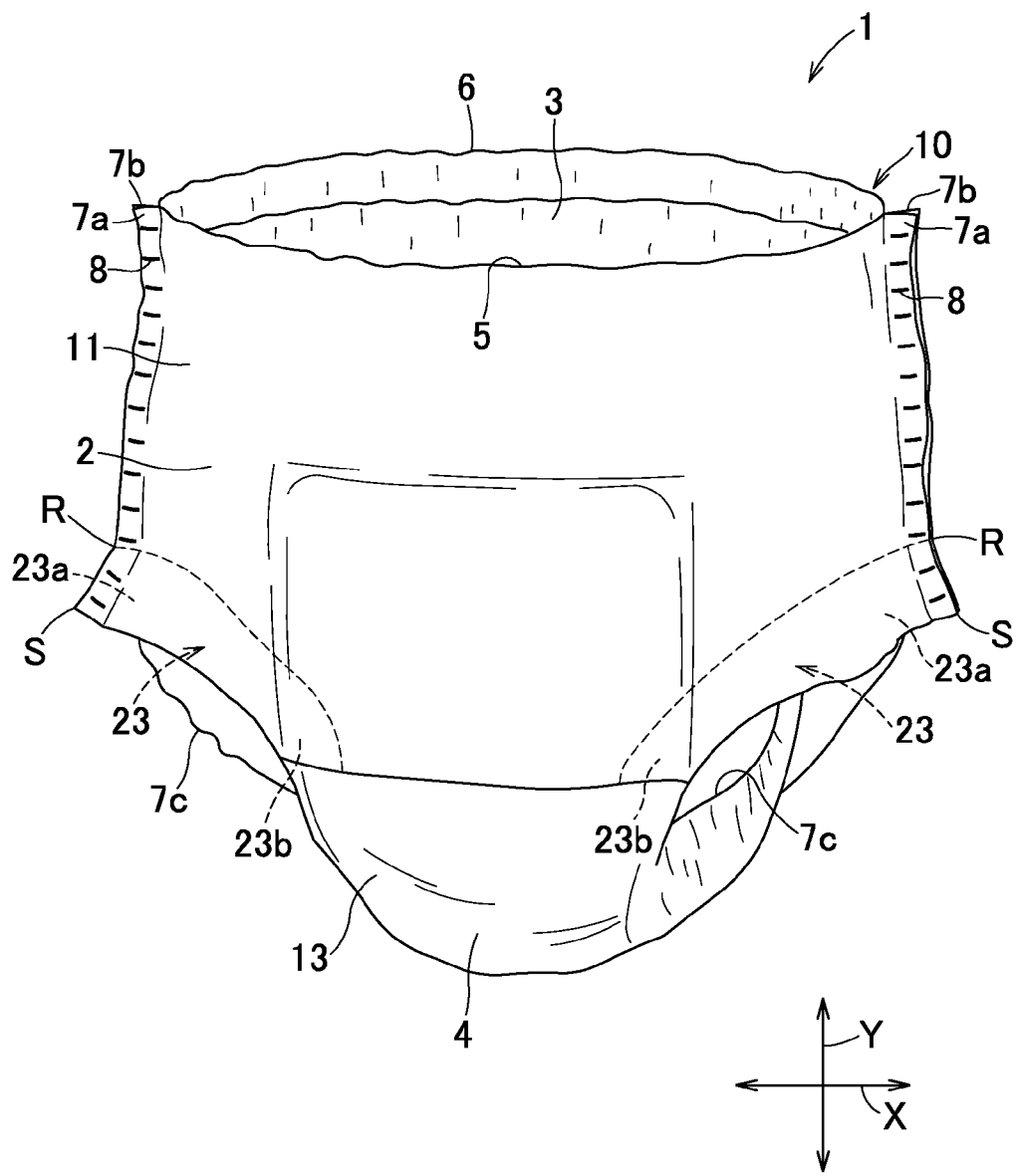
FIG. 1 is a perspective view of a diaper as a first embodiment of a disposable wearing article according to the present invention.
Figure 2:
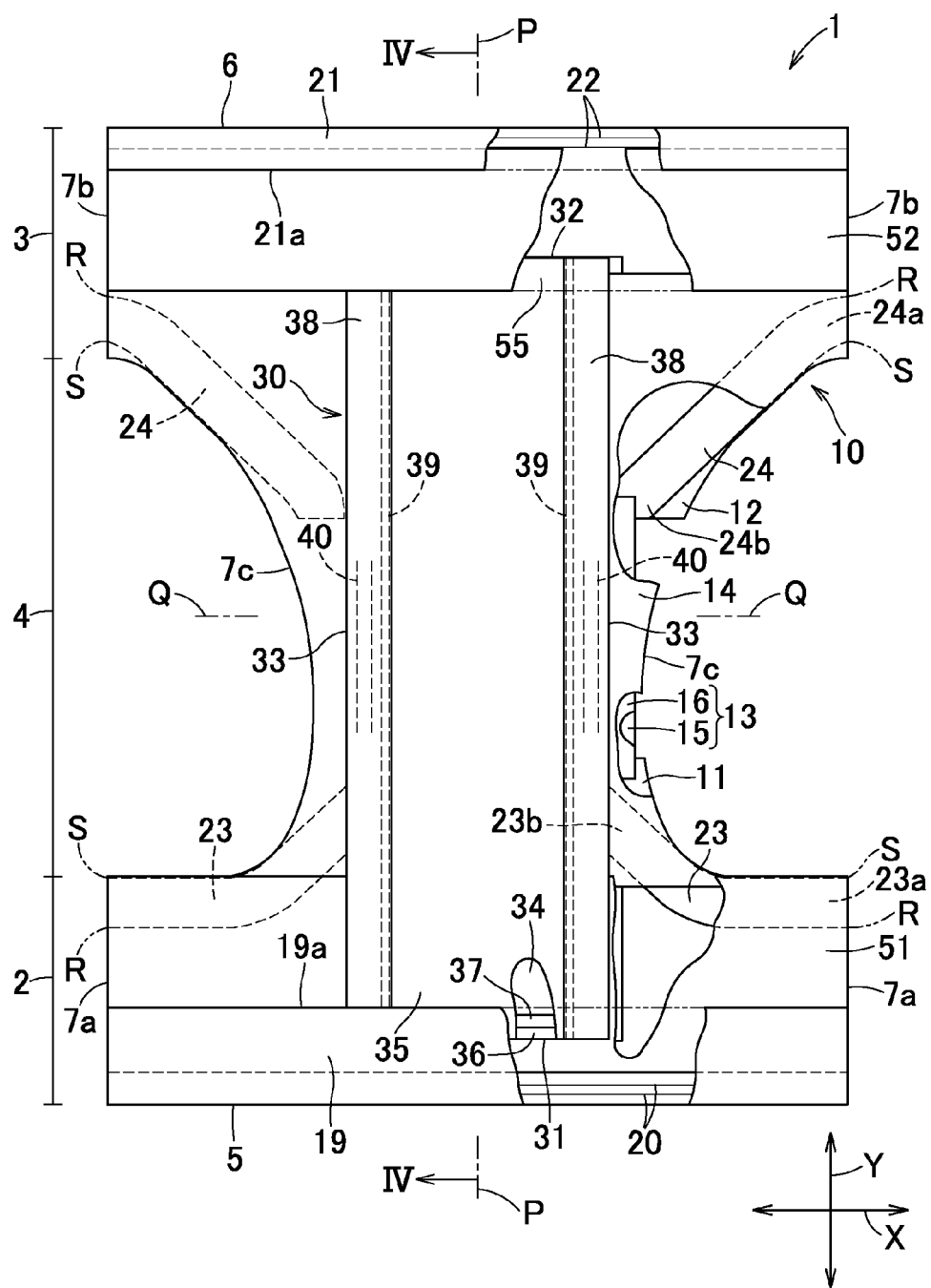
FIG. 2 is a partially cutaway developed view of the diaper.
Figure 3:
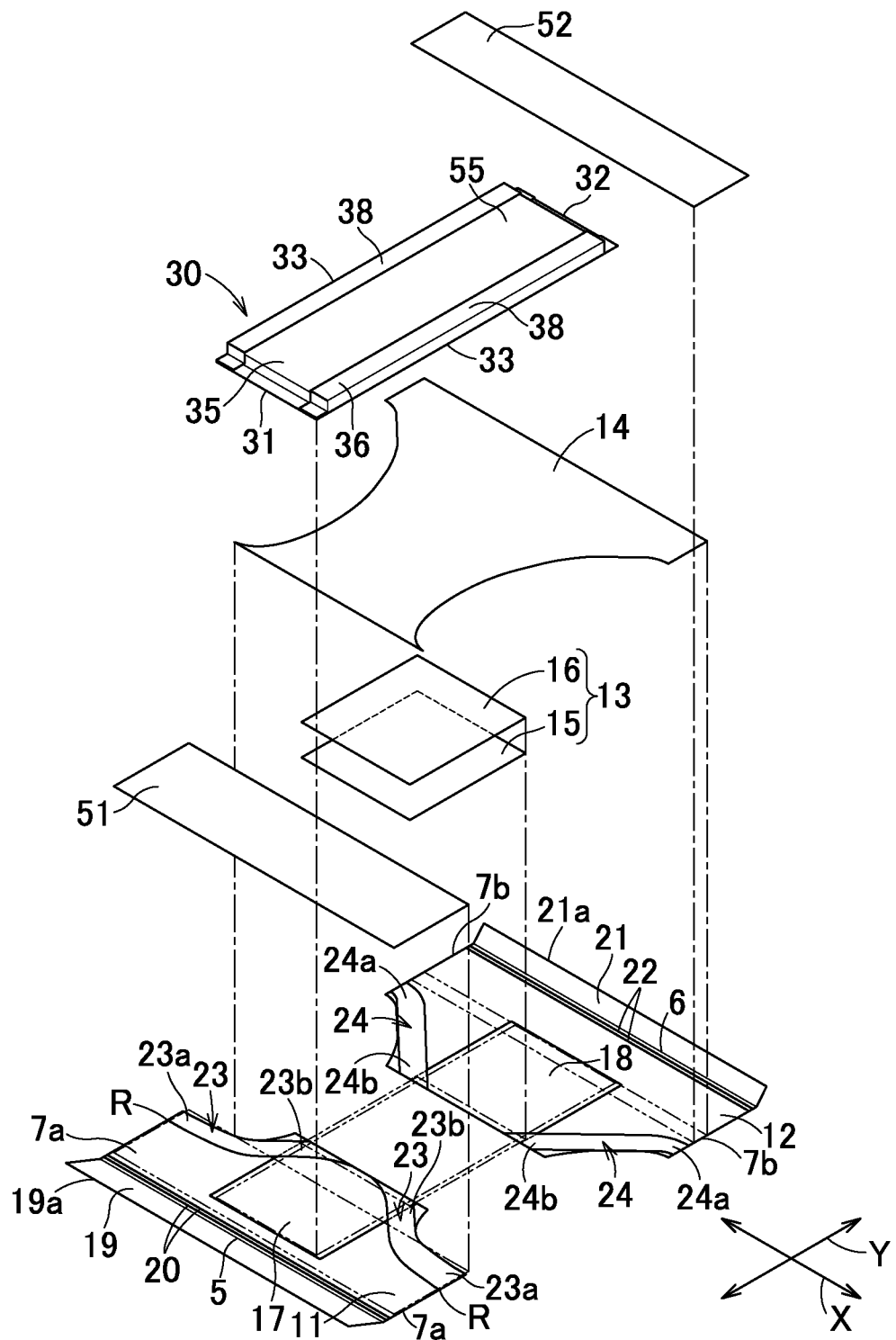
FIG. 3 is an exploded perspective view of the diaper.
Figure 4:
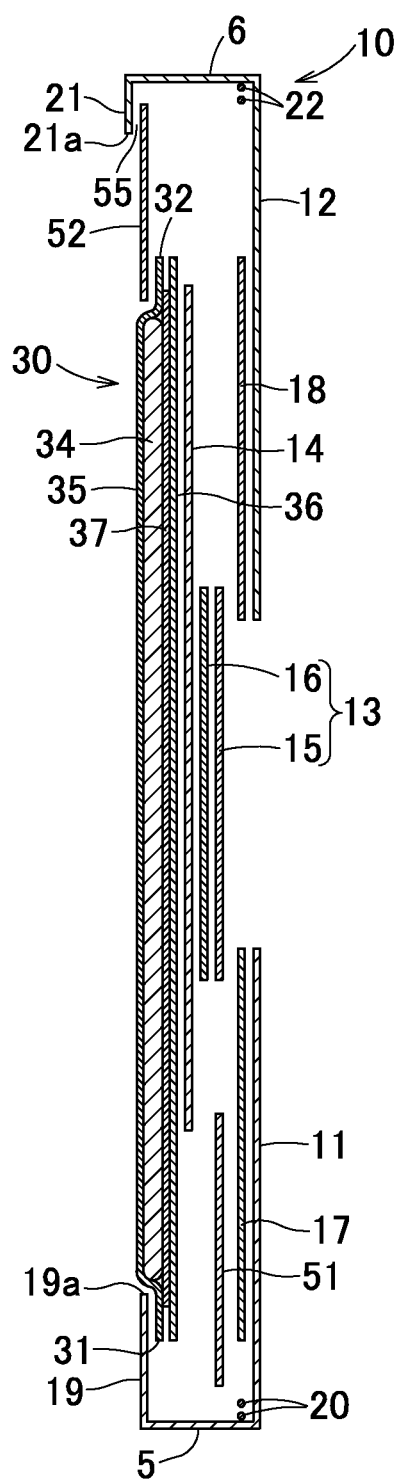
FIG. 4 is a schematic sectional view taken along the line IV-IV in FIG. 2.

FIG. 1 is a perspective view of a diaper 1 as a first embodiment of a disposable wearing article according to the present invention, FIG. 2 is a partially cutaway developed view of the diaper 1, FIG. 3 is an exploded perspective view of the diaper 1 and FIG. 4 is a schematic sectional view taken along the line IV-IV in FIG. 2. The diaper 1 has an imaginary longitudinal center line P-P bisecting a length dimension in a transverse direction X, an imaginary transverse center line Q-Q bisecting a length dimension in a longitudinal direction Y and is substantially symmetric about the imaginary longitudinal direction Y. FIGS. 2 through 4 show respective elastic elements as being stretched against contractile force thereof.

The diaper 1 includes a chassis 10 having a side facing the wearer's body and a side facing the wearer's garment so as to define an outer shape of the diaper 1 and a liquid-absorbent structure 30 attached to the side of the chassis 10 facing the wearer's body.

More specifically, the diaper 1 includes a front waist region 2, a rear waist region 3, a crotch region 4 extending between the front and rear waist regions 2, 3, front and rear ends 5, 6 opposed to each other about the imaginary transverse center line Q-Q and extending in the transverse direction X and side edges opposed to each other about the imaginary longitudinal direction P-P and extending in the longitudinal direction Y. The side edges are segmented into front waist region's side edges 7a lying in the front waist region 2, rear waist region's side edges 7b lying in the rear waist region 3 and crotch region's side edges 7c lying in the crotch region 4.

With respective elastic elements being under tension against contractile force thereof, the front waist region's side edges 7a as well as the rear waist region's side edges 7b extend substantially in parallel to the imaginary longitudinal center line P-P and the crotch region's side edges 7c are concavely curved so as to be put in close contact about the wearer's thighs. The front waist region's side edges 7a and the rear waist region's side edges 7b are joined together by lines of seams 8 arranged intermittently in the longitudinal direction Y and thereupon a waist-opening and a pair of leg-openings are formed.

The chassis 10 includes a substantially trapezoidal first backsheet 11 lying on the side facing the wearer's garment and defining the front waist region 2 and a part of the crotch region 4 and a substantially trapezoidal second backsheet 12 defining the rear waist region 3 and a part of the crotch region 4. A graphic display film sheets 17, 18 printed with graphics or the like (not shown) which can be visually recognized from the side of the wearer's garment is attached to respective inner surfaces of the first and second backsheets 11, 12.

The first and second backsheets 11, 12 are made of fibrous nonwoven fabrics. The first and second backsheets 11, 12 may respectively include two or more layers and, in this case, at least the fibrous layers defining the outer surfaces of the respective backsheets are preferably made of crimped spun bonded filament fibers. The crimped fibers used as the component fibers of the first and second backsheets 11, 12 can smoothly come in close contact with the wearer's body and contribute to improvement of texture because the crimped fibers are elastically stretchable and contractible.

The chassis 10 additionally includes an intermediate sheet 13 serving to connect the first and second backsheets 11, 12 with each other and constitutes a part of the crotch region 4. The intermediate sheet 13 includes a substantially rectangular fibrous nonwoven fabric sheet 15 lying on the side of the first and second backsheets 11, 12 and a moisture-pervious but liquid-impervious plastic sheet 16 which is the same as the fibrous nonwoven fabric sheet 15 in size as well as in shape lying on the opposite side. These two sheets 15, 16 are bonded to each other with hot melt adhesives (not shown). A fixing sheet 14 formed of a fibrous nonwoven fabric is laminated on a plastic sheet 16 to cover the intermediate sheet 13 as a whole. The fixing sheet 14 has a width dimension larger than that of the intermediate sheet 13 and extends across the crotch region 4 into the rear waist region 3. Like the first and second sheets 11, 12, the intermediate sheet 13 and the fixing sheet 14 may be formed of spun bonded fibrous nonwoven fabrics made of crimped fibers or formed of inelastic air-through fibrous nonwoven fabrics.

The front waist region 2 includes a front end flap 19 formed by folding the first backsheet 11 inward along the front end 5. The rear waist region 3 includes a rear end flap 21 formed by folding the second backsheet 12 inward along the rear end 6.

The chassis 10 as has been described above is provided on the side thereof facing the wearer's body with a liquid-absorbent structure 30 extending across the crotch region 4 into the front and rear waist regions 2, 3. The liquid-absorbent structure 30 has a horizontally long rectangular shape contoured by front and rear ends 31, 32 extending in the transverse direction X and side edges 33 extending in the longitudinal direction Y. The front end 31 overlaps the first backsheet 11, the rear end 32 overlaps the second backsheet 12 and an intermediate section between these front and rear ends 31, 32 overlaps the intermediate sheet 13.

The liquid-absorbent structure 30 includes a liquid-absorbent core 34 formed, for example, by wrapping a mixture of fluff pulp fibers and super-absorbent polymer particles with a liquid-dispersant sheet (not shown), a liner 35 lying on the side facing the wearer's body to cover an upper surface of the liquid absorbent core 34, a cover sheet 36 covering a bottom surface of the liquid-absorbent core 34 and a leakage-barrier sheet 37 made of a plastic material and sandwiched between the cover sheet 36 and the liquid-absorbent core 34.

The cover sheet 36 extends outward in the transverse direction X beyond the side edges of the liquid-absorbent core 34 and partially folded back toward the imaginary longitudinal center line P-P to form a pair of sleeve-like side flaps 38. Within the respective side flaps 38, strand-like first and second cuff elastic elements 39, 40 made of elastomer materials and extending in the longitudinal direction Y are contractibly attached under tension. The two or more first cuff elastic elements 39 lying inside as viewed in the transverse direction X extend across the crotch region 4 into the front and rear waist regions 2, 3. Under contraction of these first cuff elastic elements 39, the laterals of the cover sheet 36 are spaced from the liner 35 lying on the side facing the wearer's body to form barrier- or gasket-cuffs adapted to prevent sideways leakage of body waste. The two or more second cuff elastic elements 40 lying outboard of the first cuff elastic elements 39 as viewed in the transverse direction X are attached only to the middle zone of the crotch region 4 to form belt-like elastic zones extending along the wearer's inguinal regions. In the liquid-absorbent structure 30, the outer surface of the cover sheet 36 is fixed to the inner surface of the chassis 10 with hot melt adhesives (not shown).

As waist elastic elements to elasticize the front and rear waist regions 2, 3 of the diaper 1, first front and rear waist elastic yarns or threads 20, 22 and front and rear region elastic sheets 51, 52 are attached along the waist-opening. The first front and rear waist elastic yarns or threads 20, 22 are formed of two or more yarns or threads made of elastomer materials and contractibly attached under tension along the front and rear ends 5, 6 with hot melt adhesives (not shown) within the front and rear end flaps 19, 21 formed by folding back.

The front and rear waist elastic sheets 51, 52 are formed of elastic fibrous nonwoven fabrics containing elastomeric fibers. The front waist elastic sheet 51 lying in the front waist region 2 is sandwiched between the bottom surface of the liquid-absorbent structure 30 and the first backsheet 11 and contractibly attached under tension in the transverse direction X. The front waist elastic sheet 51 has its outer surface bonded to the first backsheet 11 with adhesives such as hot melt adhesives and its inner surface bonded to the cover sheet 36.

The rear waist elastic sheet 52 lying in the rear waist region 3 is contractibly attached under tension in the transverse direction X to the upper side of the liquid-absorbent structure 30. The rear waist elastic sheet 52 extends outward beyond the rear end 32 of the liquid-absorbent structure 30 in the longitudinal direction Y to cover the rear end 32 and extends outward also in the transverse direction X beyond the side edges 33 of the liquid-absorbent structure 30. Outboard of the liquid-absorbent structure 30 in the transverse direction X, the rear waist elastic sheet 52 and the second backsheet 12 are bonded together over a whole area thereof by bonding means such as hot melt adhesives (not shown). The front and rear waist elastic sheets 51, 52 have side edges overlapping the side edges of the first and second backsheets 11, 12, respectively.

The front and rear end flaps 19, 21 formed by folding back the first and second backsheets 11, 12 are bonded to the respective inner surfaces of the front and rear waist elastic sheets 51, 52. With an inner end 19a covering the front end 31 of the liquid-absorbent structure 30, the front end flap 19 is bonded over its whole area to the front waist elastic sheet 51 and the liquid-absorbent structure 30 by bonding means such as hot melt adhesives (not shown) to prevent component materials of the liquid-absorbent core 34 such as fluff pulp fibers from falling off.

An inner end 21a of the rear end flap 21 slightly overlaps the rear waist elastic sheet 52 and is bonded over its whole area thereto by bonding means such as hot melt adhesives (not shown).

In the diaper 1 of the construction as has been described above, the front and rear waist elastic sheets 51, 52 are contractibly provided under tension in the front and rear waist regions 2, 3, respectively, in the transverse direction X from the side edges 7a, 7b on one side to the side edges 7a, 7b on the other side. With such an arrangement, a substantially entire area of the front and rear waist regions 2, 3 can be put in contact with the wearer's body with an appropriate fit. In the front and rear waist regions provided with elastic yarns or threads arranged intermittently, these waist regions will be locally left in a non-contracted state between each pair of the adjacent elastic yarns or threads. Such a problem may be overcome by use of the front and rear waist elastic sheets 51, 52 and the waist regions can be put in close contact, over a wide range, with the wearer's body with an appropriate fit and slip down of the diaper 1 can be prevented.

Respective sections of the first and second backsheets 11, 12 defining a part of the crotch region 4 are provided with front and rear leg elastic elements 23, 24 contractibly attached under tension thereto with hot melt adhesives (not shown) along respective segments of the crotch side edges 7c. These front and rear leg elastic elements 23, 24 are formed of elasticized sheets, for example, made of elastic fibrous nonwoven fabrics containing elastomeric fibers. The fixing sheet 14 is laminated on a part of the front leg elastic elements 23 and the entirety of the rear leg elastic elements 24 to fix these elastic elements. These front and rear leg elastic elements 23, 24 serve to put the leg-openings in close contact around the wearer's legs.

One end 23a of the front leg elastic element 23 extending along the crotch side edge 7c overlaps the front waist region's side edge 7a so as to be flush therewith. The other end 23b extends into the crotch region 4. The front leg elastic element 23 is provided with the front waist elastic sheet 51 so that at least the end 23a is overlapped by the front waist elastic sheet 51. Outboard of the front waist elastic sheet 51 in the longitudinal direction Y, the first front waist elastic yarns or threads 20 are attached to the inner surface of the first backsheet 11 without overlapping the front waist elastic sheet 51.

One end 24a of the rear leg elastic element 24 extending along the crotch side edge 7c overlaps the rear waist region's side edge 7b so as to flush therewith. The other end 24b extends into the crotch region 4. Outboard of the rear leg elastic element 24 in the longitudinal direction Y, the rear waist elastic sheet 52 is attached to the inner surface of the second backsheet 12 without overlapping this rear leg elastic element 24. Outboard of the rear waist elastic sheet 52 in the longitudinal direction Y, the first rear waist elastic yarns or threads 22 are attached to the inner surface of the second backsheet 12 without overlapping this rear waist elastic sheet 52.

The front and rear leg elastic elements 23, 24 as have been described above overlap each other in a zone defined between a point R defined on the side of the waist-opening and a point S defined on the side of the leg-opening as the front and rear waist regions 2, 3 are joined together along the line of the side seams 8.

In the diaper 1 as has been described above, stiffness of the rear waist region 3 was in a range of 0.04 to 0.10 gf*cm$^2$/cm as measured in a section defined between the point R and the waist-opening and in a range of 0.16 to 0.27 gf*cm$^2$/cm as measured in a section defined between the point R and the point S. Compared to the section defined between the point R and the point S provided with the rear leg elastic element 24, none of the rear leg elastic element 24 is arranged in the section defined between the point R and the waist-opening and the measured differential stiffness may depend on existence or nonexistence of the rear leg elastic element 24.

Stiffness was measured using KES FB2 AUTO-A manufactured by KATO TECH CO., LTD. in Japan. Respective test pieces of the section defined between the point R and the waist-opening and the section defined between the point R and the point S, each having a size of 20 mm in the longitudinal direction Y×50 mm in the transverse direction X were prepared. Stiffness measurement was carried out on these test pieces with the inter-chuck distance set to 10 mm. It should be noted here that the test piece of the section defined between the point R and the point S was prepared so that the test piece extends along the rear leg elastic element 24, i.e., at an angle to the imaginary center line P-P.

While the measurement has been carried out on the test pieces prepared from the rear waist region 3, the similar measurement result will be obtained on the test pieces prepared from the front waist region 2. Specifically, stiffness of the section defined between the point R and the point S is higher than that of the section defined between the point R and the waist-opening.

On the section defined between the point R and the waist-opening and the section defined between the point R and the point S, stress generated as the respective sections are pulled in the transverse direction X was measured. For this stress measurement, AUTOGRAPH manufactured by Shimadzu Corporation in Japan was used. As test pieces, those prepared from the front waist region 2 of the diaper 1 were used. The inter-chuck distance was set to 100 mm and the inner side of the line of seams 8 on one side and the inner side of the line of seams 8 on the other side were located between these chucks. From such initial setting, the test piece was pulled by a length of 100 mm at a tension rate of 500 mm/min to measure a tensile stress and a contraction stress.

In the section defined between the point R and the waist-opening, a tensile stress of about 0.53N/20 mm was obtained and a contraction stress of about 0.10N/20 mm was obtained. In the section defined between the point R and the point S, a tensile stress of about 0.38N/20 mm was obtained and, a contraction stress of about 0.04N/20 mm was obtained. In consequence, it was determined that the stress in the section defined between the point R and the waist-opening is higher than the stress in the section defined between the point R and the point S. Also in the rear waist region 3, the stress in the section defined between the point R and the waist-opening is higher than the stress in the section defined between the point R and the point S.

Based on the measurement result, it is confirmed that the section defined between the point R and the point S and provided with the front and rear leg elastic elements 23, 24 has stiffness higher than in the section defined between the point R and the waist-opening. In consequence, the contraction of the highly stiff region in which the front and rear leg elastic elements 23, 24 overlap each other is not significant even when the first and second backsheets 11, 12 contract inward as viewed in the transverse direction X under contractile force of the first front and rear waist elastic yarns or threads 20, 22 and the front and rear waist elasticized sheets 51, 52. In other words, the section in which the front and rear leg elastic elements 23, 24 overlap each other extends further outward in the transverse direction X compared to the section defined above the point R as viewed in the longitudinal direction Y (See FIG. 1). The overlapped portion of the first and second backsheets 11, 12 has its area gradually increasing downward in the longitudinal direction Y from the point R defined by the upper ends of the front and rear leg elastic elements 23, 24, i.e., a boundary point for different levels of stiffness.

The section in which the first front and rear waist elastic yarns or threads 20, 22 are attached and defined between the point R and the waist-opening has a tensile stress in the transverse direction X is set to be higher than that in the section in which the front and rear leg elastic elements 23, 24 are attached and defined between the point R and the point S. With such differential tensile stress set in this manner, the section defined between the point R and the waist-opening can contract more easily than the section defined between the point R and the point S. In consequence, the latter section can easily broaden out- and downward.

Particularly, in the rear waist region 3, even when the rear waist elastic sheet 52 contracts, contractile force thereof exerted on the section in which the rear leg elastic elements 24 are attached is unnoticeable since the rear leg elastic elements 24 and the rear waist elastic sheet 52 do not overlap each other. As a result, the segments of the front and rear side edges 7a, 7b provided with the leg elastic elements 24 are free from noticeably contracting inward in the transverse direction X and are relatively broadened outward.

The front and rear leg elastic elements 23, 24 are attached so as to curve along the crotch side edges 7c. Upon contraction, such curved front and rear leg elastic elements 23, 24 move so as to straighten. In the course of moving, it is also supposed that the ends 23a, 24a of the front and rear leg elastic elements 23, 24 on one side may move to rotate the side of the point S outward in the transverse direction X about the point R. Assumed that the movement occurs in this manner, a distance from the base point R to the ends on the side of the crotch region is enlarged and a range of expansion also is correspondingly enlarged considering the width dimension of the front and rear leg elastic elements 23, 24 is set as wide as about 10 mm to about 40 mm. In addition, the front and rear leg elastic elements 23, 24 may be dimensioned to be relatively wide to assure that these leg elastic elements 23, 24 can be put in close contact with the wearer's body in the vicinity of the inguinal regions in a range as wide as possible and leakage of body waste such as urine can be effectively prevented. Furthermore, the crotch side edges 7c can be prevented from being soiled with body waste and from getting wrinkled.

As has been described above, the first and second backsheets 11, 12 broaden outward in the front and rear waist regions 2, 3 and therefore the leg-openings formed of the respective crotch side edges 7c are well broadened. Specifically, the locations through which the wearer's legs should be guided can be easily recognized and the diaper 1 can be smoothly put on the wearer's body. The wearer's leg should not be caught by the crotch side edge 7c.

The front and rear waist elastic sheets 51, 52 may be formed of elastic fibrous nonwoven fabrics made of heat-sealable elastomeric fibers having a basis mass in a range of 20 to 50 g/m$^2$, preferably in a range of 30 to 40 g/m$^2$ and a fiber density in a range of 0.01 to 0.04 g/cm$^3$, preferably in a range of 0.025 to 0.035 g/cm$^3$. More specifically, the sheets 51, 52 may be formed of a fiber blend composed of a thermoplastic polyurethane polymer and a thermoplastic polymer other than a thermoplastic polyurethane polymer, for example, a polyolefin polymer such as a styrene elastomer, a polyolefin elastomer, a vinyl chloride elastomer, an amide elastomer, polyethylene, polypropylene or polystyrene.

It is also possible to form the front and rear waist elastic sheets 51, 52 by a fiber blend composed of elastomeric fibers and non-elastomeric fibers. Use of the fiber blend makes it possible to alleviate the frictional effect experienced by the wearer due to the elastomeric fibers. In other words, the non-elastomeric fibers constituting the fiber blend serves to improve slippage of these front and rear waist elastic sheets 51, 52 on the wearer's skin and thereby to improve the softness as well as the texture of these front and rear waist elastic sheets 51, 52. It is also possible to adjust the stretch properties of the front and rear waist elastic sheets 51, 52.

The first and second backsheets 11, 12 are preferably formed of a heat-sealable spun bonded fibrous nonwoven fabric having a basis mass in a range of 15 to 40 g/m$^2$, preferably in a range of 25 to 35 g/m$^2$ and fiber density in a range of 0.03 to 0.10 g/cm$^3$, preferably in a range of 0.04 to 0.09 g/cm$^3$. It is also possible to form the first and second backsheets 11, 12 by two or more layers, respectively.

The front and rear leg elastic elements 23, 24 may be formed of elastic fibrous nonwoven fabric made of heat-sealable elastomeric fibers having a basis mass in a range of 20 to 50 g/m$^2$, preferably in a range of 30 to 40 g/m$^2$ and fiber density in a range of 0.01 to 0.04 g/cm$^3$, preferably in a range of 0.025 to 0.035 g/cm$^3$. More specifically, the front and rear leg elastic elements 23, 24 may be formed of a fiber blend composed of a thermoplastic polyurethane polymer and a thermoplastic polymer other than a thermoplastic polyurethane polymer, for example, a polyolefin polymer such as a styrene elastomer, a polyolefin elastomer, vinyl chloride elastomer, an amide elastomer, polyethylene, polypropylene or polystyrene. Such stretchable fibrous nonwoven fabrics may be subjected to a stretching treatment to improve stretch properties thereof. As the stretching treatment, the stretchable fibrous nonwoven fabrics may be guided to pass through between gear rolls so that further stretched regions and not further stretched regions may be formed. For example, the front leg elastic elements 23 may be treated at a gear pitch of about 2.8 mm and the rear leg elastic elements 24 may be treated at a gear pitch of about 4.9 mm. Larger the gear pitch, larger the wrinkles, leading to improvement of the texture. Smaller the gear pitch, smaller the wrinkles, leading to improvement of the adhesiveness to the other sheet.

The stretching treatment facilitates the front and rear leg elastic elements 23, 24 to be concavely curved along the crotch side edges 7c. This is because the stretch properties of these elastic elements 23, 24 are improved by the stretching treatment improves the stretch properties of these elastic elements 23, 24 and, in consequence, undesirable deflection which would be otherwise generated in the curved segments due to a differential circular arc between the inner side and the outer side of these curved segments can be prevented. Specifically, the front and rear leg elastic elements 23, 24 are not spaced from the first and second backsheets 11, 12 and can be put in close contact with the wearer's body.

The front and rear leg elastic elements 23, 24 extending along the front waist region's side edges 7a and the rear waist region's side edges 7b respectively have the ends 23a, 24a on the one side joined to the first and second backsheets 11, 12 by the side seams 8. In this manner, the ends 23a, 24a on the one side can be reliably retained. In the similar fashion, the first front and rear waist elastic yarns or threads 20, 22 and the front and rear waist elastic sheets 51, 52 also are joined to the first and second backsheets 11, 12 by the side seams 8.

Second Embodiment

Figure 5:
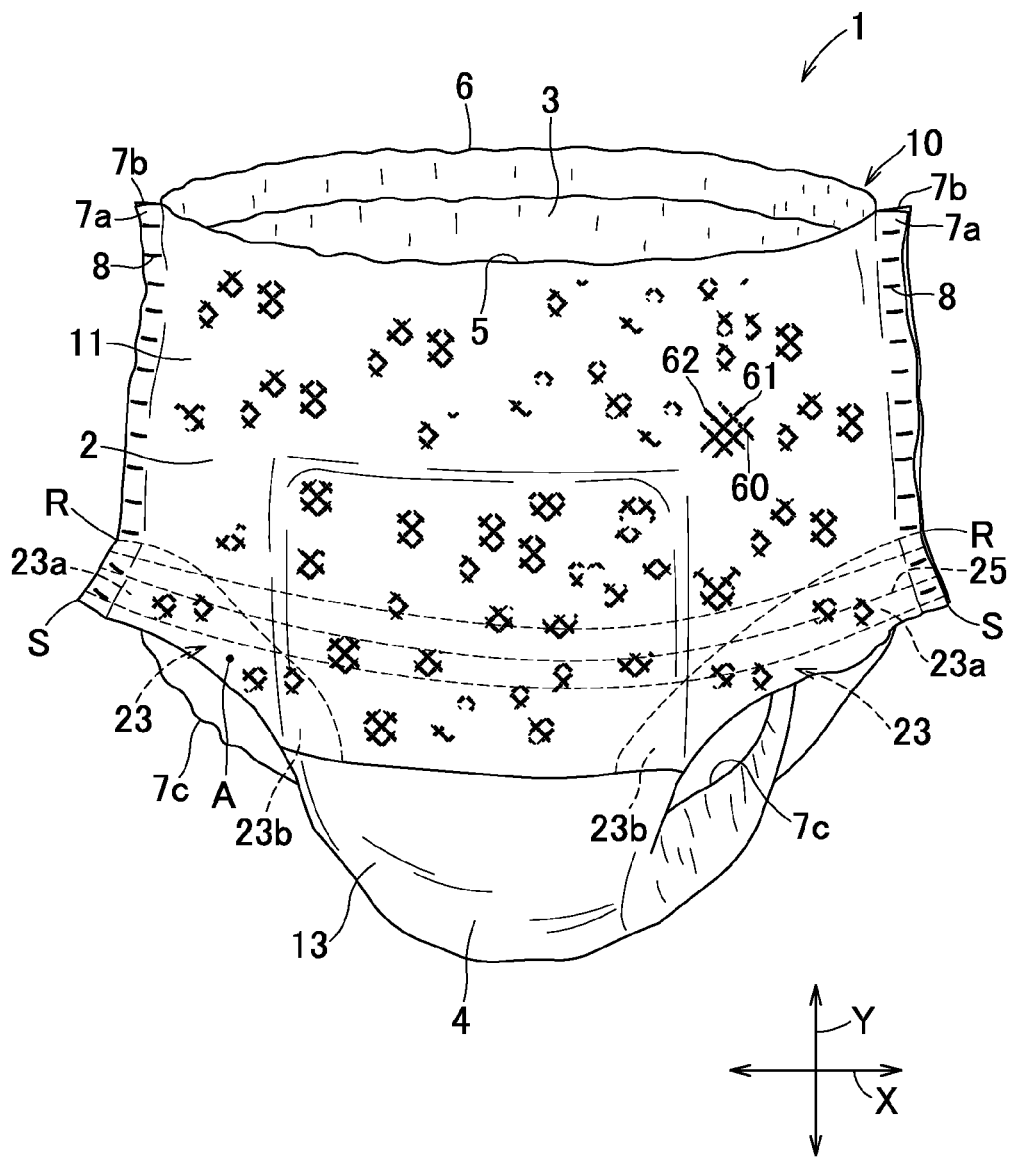
FIG. 5 is a perspective view of the diaper according to a second embodiment.
Figure 6:
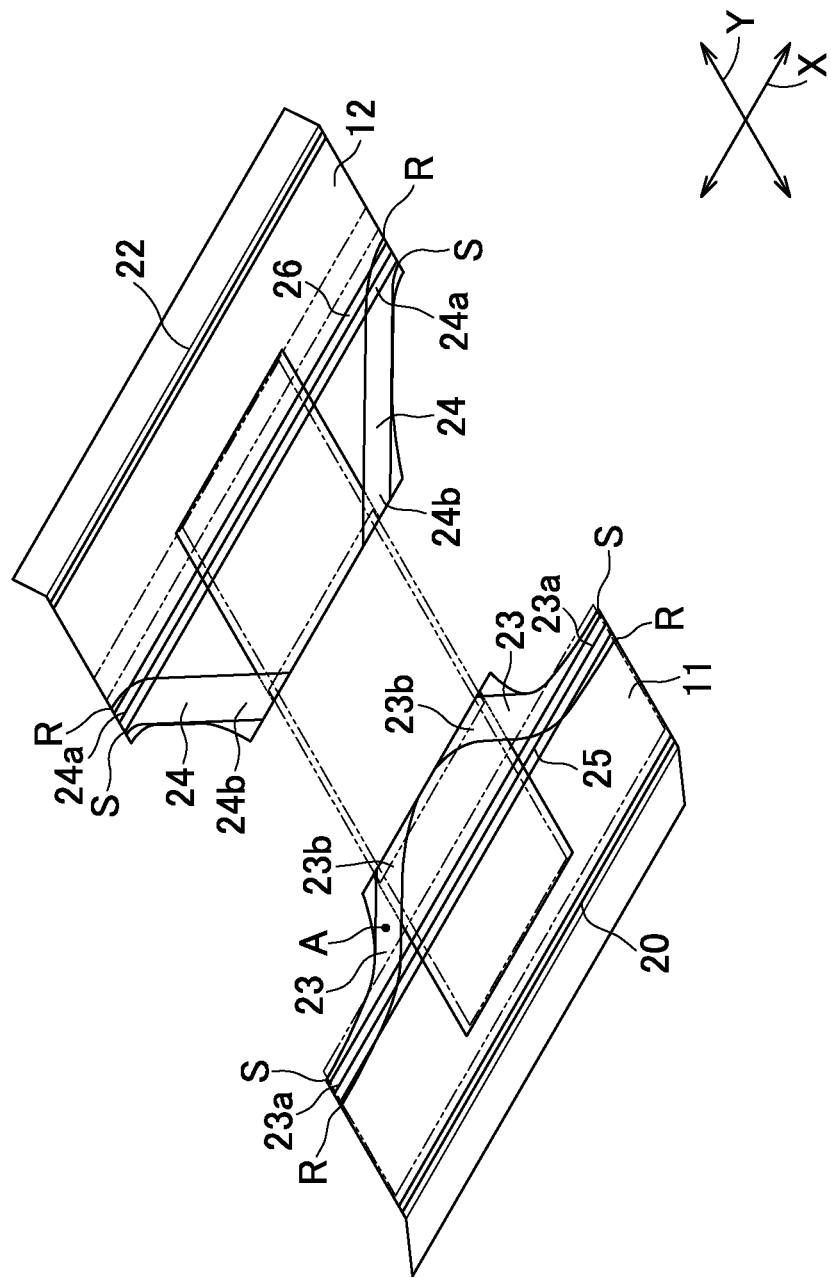
FIG. 6 is a diagram illustrating a part of the diaper shown in FIG. 5.

FIG. 5 is a perspective view of the disposable diaper 1 as a second embodiment of the disposable wearing article according to a second embodiment and FIG. 6 is a diagram illustrating apart of the diaper 1 shown in FIG. 5. The present embodiment is characterized in that the first and second backsheets 11, 12 respectively have a plurality of thermal compression bonded regions 60 and second front and rear waist elastic yarns or threads 25, 26 formed of elastomeric yarns or threads as the waist elastic elements. The other features are similar to those in the first embodiment, therefore, these similar component elements are designated by similar reference numerals and detailed description thereof will be eliminated.

According to the second embodiment, the first and second backsheets 11, 12 are formed of heat-sealable crimped spun bonded filament fibers. The first and second backsheets 11, 12 are locally subjected to a thermal compression bonding process from respective outer surfaces toward respective inner surfaces to form a plurality of thermal compression bonded regions (debossed regions) 60. In each of the thermal compression bonded regions 60, the respective outer surfaces of the backsheets 11, 12 are thermal compression bonded by embossing rolls or the like so that the crimped fibers are compressed in the thickness direction of the backsheets 11, 12. These many thermal compression bonded regions 60 are intermittently formed in given two directions to define first thermal compression bonding lines 61 and second thermal compression bonding lines 62. Specifically, these first thermal compression bonding lines and second thermal compression bonding lines 62 are respectively disposed to intersect with one another and to extend at an angle to the imaginary transverse center line Q-Q. These first and second thermal compression bonding lines 61, 62 are formed over the entire areas of the first and second backsheets 11, 12. For convenience of illustration, these thermal compression bonding lines 61, 62 are partially left off in FIG. 5.

The first and second backsheets 11, 12 are provided on respective inner surfaces thereof with the front and rear waist elastic sheets 51, 52 contractibly attached thereto under tension. With such an arrangement, the first and second backsheets 11, 12 contract in the transverse direction X as the front and rear waist elastic sheets 51, 52 contract. In consequence, these first and second backsheets 11, 12 are formed between respective pairs of the adjacent thermal compression bonded regions 60 with raised ridges. The raised ridges formed in this manner make the first and second backsheets 11, 12 bulky appropriately for airy and soft texture. The thermal compression bonded regions 60 may be selectively designed to have any one of various patterns such as a dot-like shape, a linear shape and a rectangular shape.

Referring to FIG. 6, the first and second backsheets 11, 12 are provided on respective inner surfaces thereof with the second front and rear waist elastic yarns or threads 25, 26 contractibly attached thereto under tension, respectively. The second front and rear waist elastic yarns or threads 25, 26 at least partially overlap the front and rear leg elastic elements 23, 24 and extend in the transverse direction X. Respective opposite ends of the second front and rear waist elastic yarns or threads 25, 26 lie on the associated lines of side seams 8. The second front and rear waist elastic yarns or threads 25, 26 are attached to the first and second backsheets 11, 12 in zones of the front and rear waist regions 2, 3 defined in the vicinity of respective boundary lines to the crotch region 4 so as to extend substantially in parallel to the first front and rear waist elastic yarns or threads 20, 22. Consequentially, the second front and rear waist elastic yarns or threads 25, 26 overlap the ends 23a, 24a of the front and rear leg elastic elements 23, 24 extending into the front and rear waist regions 2, 3 but are spaced from the ends 23b, 24b lying in the crotch region 4 in the longitudinal direction Y.

Respective sections of the front and rear waist regions 2, 3 in which the second front and rear waist elastic yarns or threads 25, 26 overlap the front and rear leg elastic elements 23, 24 are broadened outward in the transverse direction X and downward (i.e., toward the crotch region 4) as the first embodiment is the case. According to the present embodiment, the second front and rear waist elastic yarns or threads extend in the transverse direction X across the respective sections defined between the points R and the points S function to make the curves starting from the respective points R smooth and thereby to prevent the wearer's legs from being caught or interrupted by the sections broadened out in the transverse direction X. On the other hand, at least in the vicinity of the points R, the contractile force of the second front and rear waist elastic yarns or threads 26, 26 and the front and rear waist elastic sheets 51, 52 assure the front and rear leg elastic elements 23, 24 to be put in close contact with the wearer's body. In this way, a gap should not be left between these front and rear leg elastic elements 23, 24 and the wearer's body and body waste such as urine should not leak out of the diaper 1 through such gap.

In the diaper 1 according to the first embodiment as well as in the diaper 1 according to the second embodiment, the elasticized sheets such as those made of fibrous nonwoven fabrics are used as the front and rear leg elastic elements 23, 24 to assure a larger contact area of the diaper 1 to the wearer's body along the leg-openings than the case in which strand-like elastic yarns or threads are used for the same purpose. By assuring larger contact area, it is possible to reduce the contact pressure per unit area of the wearer's skin. The contact surface pressure to the wearer's skin, the rubber impression left on the wearer's skin and the amylase activity in the wearer's saliva were measured on the diaper 1 according to the second embodiment selected as the Inventive Example and a diaper 100 using strand-like elastic yarns or threads as the front and rear leg elastic elements selected as the Comparative Example.

Comparative Example

Figure 7:
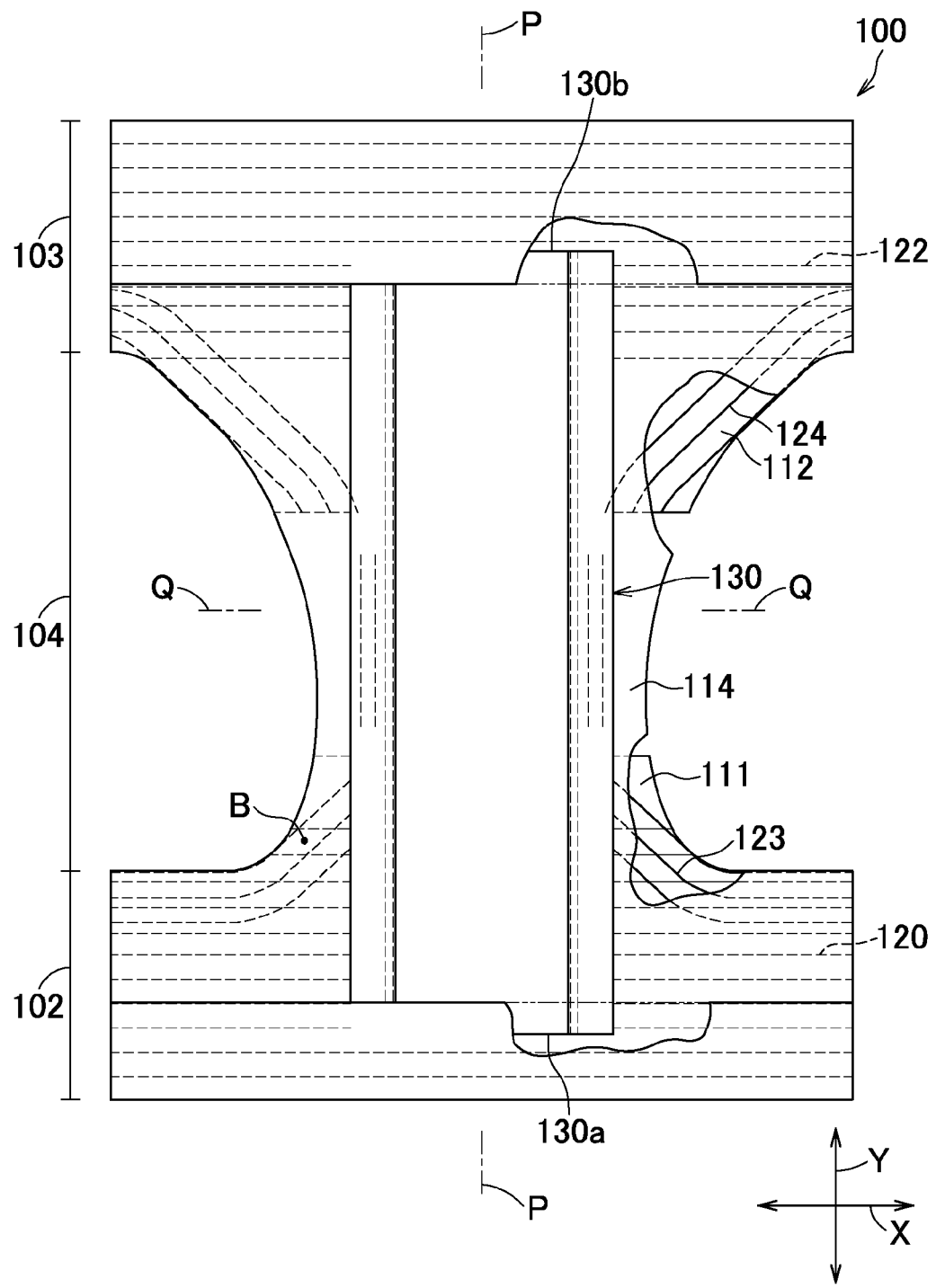
FIG. 7 is partially cutaway developed view of the diaper according to a comparative embodiment.
Figure 8:
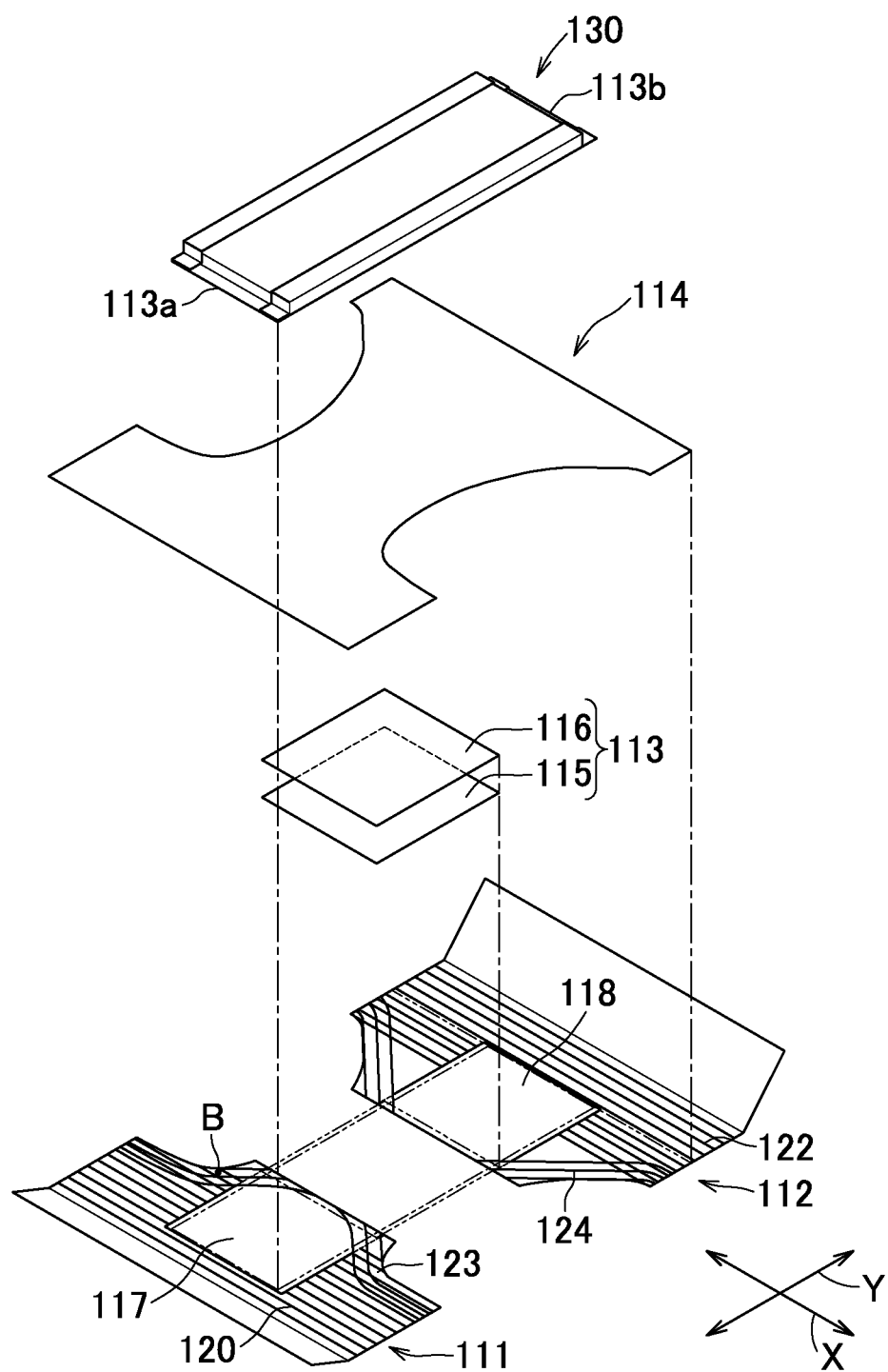
FIG. 8 is an exploded perspective view of the comparative embodiment.

FIG. 7 is partially cutaway developed view of the diaper 100 as Comparative Example and FIG. 8 is an exploded perspective view of the Comparative Example both being illustrated with the respective elastic elements under tension against the contractile force thereof. As illustrated, the diaper 100 as the Comparative Example includes first and second backsheets 111, 112 both facing the wearer's garment, and a topsheet 114 lying on the side of the first and second backsheets 111, 112 facing the wearer's body. Between the first and second backsheets 111, 112 and the topsheet 114, graphic display film sheets 117, 118 printed with graphics (not shown) adapted to be visually recognized from the side facing the wearer's garment are attached.

The first and second backsheets 111, 112 are arranged so as to be spaced from each other in the longitudinal direction Y and an intermediate sheet 115 interposed between these two backsheets 111, 112 wherein the intermediate sheet 113 includes a fibrous nonwoven fabric sheet 115 and an moisture-pervious but liquid-impervious plastic sheet 116 both having a substantially rectangular shape and bonded to each other. The topsheet 114 overlaps the first and second backsheets 111, 112 and the intermediate sheet 113. The first and second backsheets 111, 112 and the topsheet 114 are formed of an air-through fibrous nonwoven fabric having no elastic stretch property.

A liquid-absorbent structure 130 is attached to the side of the topsheet 114 facing the wearer's body and the first and second backsheets 111, 112 are folded back inward in the longitudinal direction Y thereof so as to cover front and rear ends 130a, 130b of the liquid-absorbent structure 130. A plurality of strand-like front and rear waist elastic yarns or threads 120, 122 are attached between the first and second backsheets 111, 112 and the topsheet 114. These front and rear waist elastic yarns or threads 120, 122 are attached under tension and in a contractible manner so as to extend in the transverse direction X. These front and rear waist elastic yarns or threads 120, 122 are arranged so that the contractile force thereof in a region overlapping the liquid-absorbent structure 130 is not exerted on this liquid-absorbent structure 130. Between the first and second backsheets 111, 112 and the topsheet 114, a plurality of strand-like front and rear leg elastic yarns or threads 123, 124 are contractibly attached under tension along respective ends both adjacent to the crotch region 104. The opposite side edges of the front waist region may be joined to the respectively associated opposite side edges of the rear waist region to obtain the diaper 100 as shown in FIG. 1.

<Measuring Method for Contact Surface Pressure>

On the diaper according to the second embodiment of the present invention and a diaper selected as Comparative Example, contact surface pressure to the wearer was measured. The measurement was conducted by putting the respective diapers as Inventive Example and Comparative Example on an infant-shaped doll having movable hip joints. For the measurement, Air-Pack Type Contact Surface Pressure Measuring System (manufactured by AMI TECHNO CO., LTD. in Japan) was used. Specifically, with an air-pack having a diameter of 20 mm attached to the doll, oppressiveness varying as the doll's posture changes was measured as contact surface pressure (hPa). For the Inventive Example, the air-pack was attached to the region overlapping the front leg elastic elements 23 but not the second front waist elastic yarns or threads 25. More specifically, the air-pack was attached to the surface of the doll on which the point A is present when the diaper 1 has been put on. In Comparative Example, the point B corresponds to the point A of Inventive Example and is present in the region overlapping the front leg elastic yarns or threads 123 and the front waist elastic yarns or threads 120.

After the air-pack had been attached to the doll, the diaper of Inventive Example or Comparative Example was put on the doll and the contact surface pressure was measured as the doll's posture was successively changed into four (4) postures. The contact surface pressure was measured five (5) times per one second and the maximum value was recorded as the contact surface pressure Pm in respective postures. The contact surface pressure Pm was measured ten (10) times and an average thereof was recorded as the contact surface pressure P for each posture. The doll was provided substantially in center of its upper body with a trunk axial rod and substantially in centers of the respective thighs with thigh's axial rod.

(1) Leg Cocked Posture:

From the posture lying face up, doll's legs was repetitively cocked three (3) times and the contact surface pressure Pm was measured. The doll's legs were cocked so that the thighs axial rods swing at an angle of about 100° to the floor surface at a cocking rate of about 80°/sec. An angle between a pair of the thigh axial rods was set to about 60°. As the contact surface pressure Pm, the maximum value in the course of cocking the thigh axial rods to the angle of about 100° to the floor surface was recorded.

(2) Seated Posture:

The seated posture is defined by the posture in which the trunk axial rod of the doll is at an angle of about 90° to the floor surface. In this posture, the angle between the thigh axial rods was set to about 30°. The doll was left in this seated posture for about five (5) seconds and the maximum value measured during 5 seconds was recorded as the contact surface pressure Pm.

(3) Upright Posture:

The contact surface pressure Pm when the doll was in upright posture was measured. The upright posture was defined in this measuring operation by the posture in which the thigh axial rods was at an angle of about 90° to the floor surface and the trunk axial rod was at an angle of about 100°. Specifically, the doll was in slightly droopy posture. The doll was left in this upright posture for about five (5) seconds and the maximum value measured during such five (5) seconds as recorded as the contact surface pressure Pm.

(4) Walking Posture:

The legs of the doll were alternately moved as if the doll walks and the contact surface pressure generated during five (5) steps was measured as the contact surface pressure during walking. More specifically, one of the thigh axial rods was moved forward from the above-mentioned upright posture. At this moment, the one thigh axial rod was at an angle of about 20° between a vertical line to the floor surface with the other thigh axial rod at an angle of about 10° to this vertical line. Then, the other thigh axial rod was moved forward at an angle of about 20° with the one thigh axial rod at an angle of about 10°. Such movement was repeated five (5) times to simulate the walking. A movement rate was set to 70°/sec and five (5) peak values were measured from five (5) times repeated movements and an average value thereof was recorded as the contact surface pressure Pm.

<Measurement Result for Contact Surface Pressure>

Measurement result for the above-mentioned postures (1)-(4) are indicated in TABLE 1. As will be apparent from TABLE 1, the contact surface pressure measured on Inventive Example is lower than that measured on Comparative Example with respect to all postures. The leg-openings of the diaper may often bite into the wearer's inguinal regions as the wearer's body moves. The wearer's inguinal regions correspond to the region of the doll to which the air-pack was attached for measurement of the contact surface pressure. However, the contact surface pressure may be reduced as has been demonstrated by Inventive Example to alleviate irritation by the leg-openings and to achieve comfortable feeling to wear the diaper.

TABLE 1

| | Contact Pressure P | |
|---|---|---|
| Doll's posture | Inventive Example (hPa) | Comparative Example (hPa) |
| (1) Leg cocked posture | 16 | 33 |
| (2) Seated posture | 15 | 30 |
| (3) Upright posture | 8 | 23 |
| (4) Walking posture | 8 | 22 |

<Measuring Method for Rubber's Impression>

Rubber's impression left by the respective diapers according to Inventive Example and Comparative Example around the wearer' legs was measured. Measurement of rubber's impression was conducted by putting the respective diapers according to Inventive Example and Comparative Example on five (5) infants. More specifically, after the respective diapers had been put on these infants for about 15 to 18 hours from the bedtime to the next day, the regions about the wearer's legs corresponding to the point A of the diaper 1 as Inventive Example and the regions around the wearer's legs corresponding to the point B of the diaper 100 as Comparative Example were photographed by a digital camera and thereby erythema index in these regions were measured. As wearers, i.e., subjects, two (2) male infants and three (3) female infants were selected. From the bedtime at which the diaper had been put to the time of measurement, the diaper was exchange about four (4) times. For measurement with Inventive Example, the used diaper 1 according to Inventive Example was exchanged with fresh diaper 1 according to Inventive Example and for measurement with Comparative Example, the used diaper 100 according to Comparative Example was exchanged with fresh diaper 100 according to Comparative Example.

Erythema index was determined by analyzing the photographed digital image using Image J (manufactured by National Institute of Health in the United States). Erythema index is a value defined by absorbance difference of wavelength in green region (G) and red region (R) of skin. Specifically, the erythema index can be obtained on the basis of calculated logarithmic image difference represented by an equation of $\log(1/G)-\log(1/R)=\log G-\log R$.

<Measurement Result for Rubber's Impression>

Figure 9:
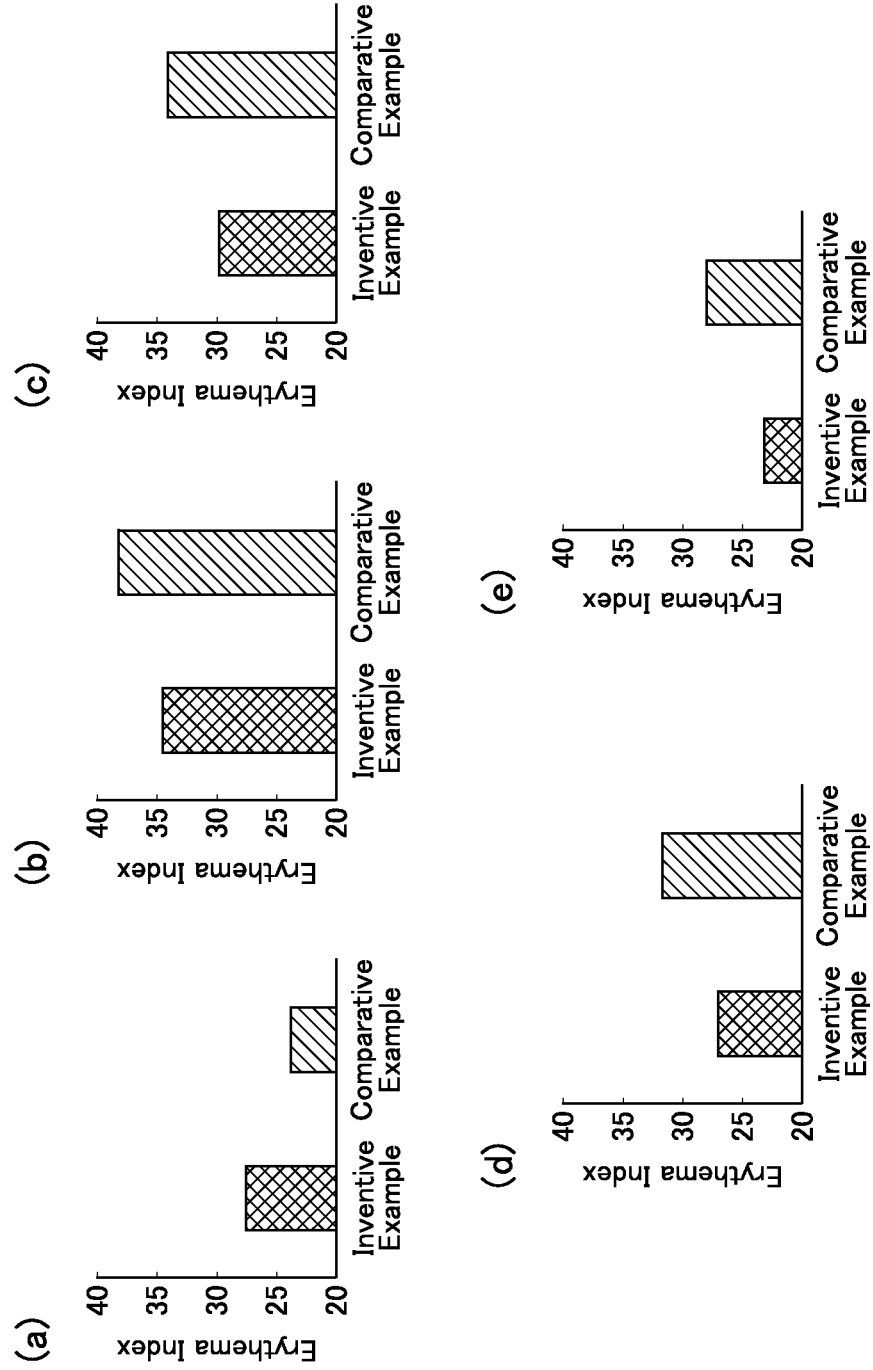
FIGS. 9(a)-9(e) are graphic diagrams indicating erythema indices measured on the wearers a-e.

The measurement result is indicated by FIG. 9. FIG. 9(a)-FIG. 9(e) are graphic diagrams indicating the measurement result of the erythema indices obtained from the wearers (subjects) a-e having worn the diapers according to Inventive Example or Comparative Example. As will be apparent from FIG. 9, in the wearers b, c, d, e except the wearer a, the erythema indices due to the diaper 1 according to Inventive Example were milder than the erythema indices due to the diaper 100 according to Comparative Example. From this measurement result, it was suggested that the contact surface pressure may be alleviated to alleviate uncomfortable irritation to the skin the wearer might experience.

<Measuring Method for Amylase Activity>

In the human body, an amount of amylase contained in saliva increases as the sympathetic nerve system is stimulated by factors such as stress. In view of this, the amylase activity in saliva was measured as an index indicating a stressed degree of the wearer. The amylase activity was measured using Saliva Amylase Monitor (manufacture by NIPRO in Japan) as an enzyme analyzer. As the wearers (subjects), twenty nine (29) infants who were 16.4+/−2.9 months old were selected for measurement of amylase activity. Specifically, after three (3) minutes with no diaper put on, the diapers according to Inventive Example or Comparative Example were put on the subjects further for three (3) minutes and, immediately thereafter, the amylase activity in saliva of the wearers were measured.

<Measurement Result for Amylase Activity>

The measurement result of amylase activity indicated that the amylase activity, i.e., stimulation of the sympathetic nerve system is lower when the wearer uses the diaper 1 according to Inventive Example than the amylase activity when the wearer uses the diaper 100 according to Comparative Example. Therefore, the diaper 1 according to Inventive Example effectively alleviates the stress affecting the wearer and creates a comfortable feeling to the wearer.

As materials for the respective component members or elements of the elasticized waist panel 11 and the crotch member 12 are not limited to those which have been described with respect to the first and second embodiments of the present invention and the other various materials widely used in the related technical field may be selectively used without departing from the scope of the present invention. The present invention may be implemented in the form of a diaper 1 having the front waist region 2, the rear waist region 3 and the crotch region 4 which are continuously formed.

The terms "first" and "second" used in the specification and the appended Claims should be construed to be used for the purpose of merely discriminating elements and/or positions of the same appellation. For example, the term "first waist region" used herein means one of the front and rear waist regions and the term "second waist region" means the other thereof.

REFERENCE SIGNS LIST 1 diaper (disposable wearing article)
2 front waist region (first or second waist region)
3 rear waist region (first or second waist region)
4 crotch region
8 side seams
10 chassis
11 first backsheet (backsheet)
12 second backsheet (backsheet)
20 first front waist elastic yarns or threads
22 first rear waist elastic yarns or threads
23 front leg elastic elements
23a one end
23b other end
24 rear leg elastic elements
24a one end
24b other end
25 second front waist elastic yarns or threads
26 second rear waist elastic yarns or threads
51 front waist elasticized sheet
52 rear waist elasticized sheet
60 thermal compression bonded regions

The invention claimed is:

1. A disposable wearing article having a longitudinal direction, a transverse direction, and a thickness direction, said disposable wearing article comprising:
a chassis comprising a side adapted to face a wearer's body, a side adapted to face away from the wearer's body, a first waist region which is one of front and rear waist regions, a second waist region which is the other of the front and rear waist regions, and a crotch region extending between the first and second waist regions;
waist elastic elements configured to contractibly elasticize the first and second waist regions in the transverse direction; and
leg elastic elements configured to contractibly elasticize the crotch region in the longitudinal direction,
wherein
the first and second waist regions are joined together along respective opposite side edges thereof to form lines of side seams having a stiffness higher than a remaining region of the first and second waist regions and to form a waist-opening and a pair of leg-openings,
the leg elastic elements are formed of elasticized sheets each having opposite ends at least one of which overlaps associated one of the opposite side edges and having a stiffness higher than the remaining region,
a contractile force of the waist elastic elements is greater than that of the leg elastic elements so that sections of the first and second waist regions adjacent the crotch region and overlapping the leg elastic elements are broadened outward in the transverse direction,
the waist elastic elements comprise
first waist elastic yarns or threads formed of elastomeric elastic yarns or threads attached along the waist-opening; and
waist elastic sheets arranged closer to the crotch region than the first waist elastic yarns or threads and formed of elasticized sheets,
the waist elastic sheet arranged in the front waist region overlaps the leg elastic elements in the thickness direction, and
the waist elastic sheet arranged in the rear waist region is located in the longitudinal direction between (i) the first waist elastic yarns or threads and (ii) the leg elastic elements, without overlapping the leg elastic elements in the thickness direction.

2. The disposable wearing article defined by claim 1, wherein the leg elastic elements comprise:
front leg elastic elements extending from the front waist region to the crotch region, wherein the waist elastic sheet arranged in the front waist region overlaps the front leg elastic elements in the thickness direction; and
rear leg elastic elements extending from the rear waist region to the crotch region, wherein the waist elastic sheet arranged in the rear waist region does not overlap the rear leg elastic elements in the thickness direction.

3. The disposable wearing article defined by claim 1, wherein the leg elastic elements are formed of a stretchable fibrous nonwoven fabric including elastomeric fibers.

4. The disposable wearing article defined by claim 1, wherein the chassis and the leg elastic elements are joined together by the lines of side seams.

5. The disposable wearing article defined by claim 4, wherein
the waist elastic elements further include second waist elastic yarns or threads formed of elastic yarns or threads overlapping the leg elastic elements in the front and rear waist regions and extending in the transverse direction up to the side seams, and
in each of the front and rear waist regions, the waist elastic sheet is arranged in the longitudinal direction between (i) the corresponding first waist elastic yarns or threads and (ii) the corresponding second waist elastic yarns or threads.

6. The disposable wearing article defined by claim 5, wherein
each of the waist elastic sheets has a dimension in the longitudinal direction greater than that of each of the first waist elastic yarns or threads, and
each of the waist elastic sheets has the dimension in the longitudinal direction greater than that of each of the second waist elastic yarns or threads.

7. The disposable wearing article defined by claim 1, wherein
the chassis includes backsheets lying on the side adapted to face away from the wearer's body, and
the backsheets include crimped fibers and are formed with a plurality of thermal compression bonded regions.

8. The disposable wearing article defined by claim 1, wherein
the waist elastic sheets include a first waist elastic sheet in the first waist region, and a second waist elastic element in the second waist region, and
the first waist elastic sheet is located on the side adapted to face away from the wearer's body, and the second waist elastic element is located on the side adapted to face the wearer's body.

* * * * *